United States Patent
Meier et al.

(10) Patent No.: US 7,504,510 B2
(45) Date of Patent: Mar. 17, 2009

(54) GRAFTABLE HINDERED AMINE LIGHT STABILIZERS

(75) Inventors: Hans-Rudolf Meier, Basel (CH); Gerrit Knobloch, Magden (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 489 days.

(21) Appl. No.: 10/543,428

(22) PCT Filed: Feb. 2, 2004

(86) PCT No.: PCT/EP2004/050068

§ 371 (c)(1), (2), (4) Date: Jul. 26, 2005

(87) PCT Pub. No.: WO2004/072035

PCT Pub. Date: Aug. 26, 2004

(65) Prior Publication Data

US 2006/0173107 A1 Aug. 3, 2006

(30) Foreign Application Priority Data

Feb. 14, 2003 (EP) .................................. 03405085

(51) Int. Cl.
*C07D 211/00* (2006.01)
*C08K 5/34* (2006.01)

(52) U.S. Cl. ...................................... 546/186; 524/103
(58) Field of Classification Search ................. 546/186; 524/103
See application file for complete search history.

(56) References Cited

U.S. PATENT DOCUMENTS

| 4,429,077 A | 1/1984 | Karrer et al. ................. 525/143 |
| 4,684,726 A | 8/1987 | Greco et al. ................... 544/69 |
| 4,952,619 A * | 8/1990 | Greco et al. ................... 524/96 |
| 4,977,259 A * | 12/1990 | Greco et al. ................... 544/69 |
| 4,981,915 A | 1/1991 | MacLeay et al. ......... 525/327.6 |
| 7,160,955 B2 * | 1/2007 | Meier et al. .............. 525/331.8 |
| 2004/0152836 A1 | 8/2004 | Meier et al. .................... 525/65 |

OTHER PUBLICATIONS

English language abstract for DE 19625287 (Jan. 2, 1998).

* cited by examiner

*Primary Examiner*—D. Margaret Seaman
*Assistant Examiner*—Nizal S Chandrakumar
(74) *Attorney, Agent, or Firm*—Tyler A. Stevenson

(57) ABSTRACT

The invention describes novel compound of the formula (I), wherein the general symbols are as defined in claim 1, as stabilizers for protecting organic materials, in particular synthetic polymers, against oxidative, thermal, dynamic, light-induced and/or ozone-induced degradation.

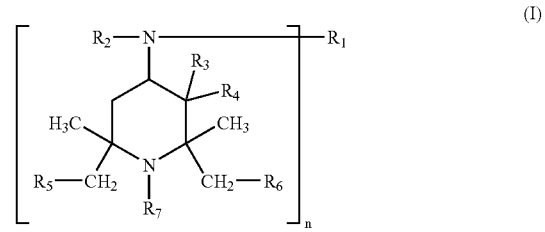

(I)

15 Claims, No Drawings

GRAFTABLE HINDERED AMINE LIGHT STABILIZERS

The present invention relates to novel hindered amine light stabilizers which are graftable onto organic materials and to compositions comprising an organic material which is susceptible to oxidative, thermal, dynamic, light-induced and/or ozone-induced degradation, and such novel compounds and optionally further additives. The present invention relates also a method of stabilizing organic materials against oxidative, thermal, dynamic, light-induced and/or ozone-induced degradation using such novel graftable hindered amine light stabilizers and to a method of grafting the novel hindered amine light stabilizers onto organic materials, preferably synthetic polymers.

A customary method of stabilizing and modifying polymers and their properties is reactive extrusion. In that method, additives are added to the thermoplastic polymer during extrusion in order to modify the properties of the polymer. That can be accomplished, for example, by grafting an unsaturated compound onto the polymer. Such reactive grafting processes are customarily performed by the combined use of an unsaturated compound and a peroxide as a free-radical-former. When the polymer is modified with functional monomers, for example maleic anhydride, copolymers are obtained that are used as compatibilizers (compatibility promoters) or adhesion promoters.

Current methods have crucial disadvantages, however, which are attributable to the use of peroxides as free-radical-formers. Whilst undesirable subsidiary reactions influence the processing characteristics of the polymers (depending on the type of polymer used there may occur, for example, cross-linking/gel formation or polymer degradation), reaction products of the peroxide and peroxide residues cause a deterioration in the long-term stability of the polymer. Furthermore, considerable safety precautions have to be taken in the case of polymer processing with the addition of peroxides.

WO-A-02/081432 discloses that polymers grafted with sulfoxides of sulfones have outstanding stability against oxidative, thermal, dynamic, light-induced and/or ozone-induced degradation.

However, these known grafting agents do not in every respect satisfy the high requirements expected of a grafting agent, especially in respect of storage stability, water absorption, sensitivity to hydrolysis, stabilization during processing, long-term stabilization, colour characteristics, volatility, migration characteristics, compatibility and especially light stabilization. There is therefore still a need for effective grafting agents for organic materials that are sensitive to oxidative, thermal, dynamic, light-induced and/or ozone-induced degradation.

It has now been found that a specific group of novel hindered amine light stabilizers are especially well suited as grafting agents for organic materials, especially polymers, that are sensitive to oxidative, thermal, dynamic, light-induced and/or ozone-induced degradation.

The present invention accordingly relates to novel compounds of the formula I

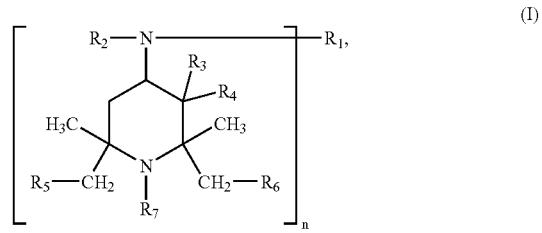

wherein, when n is 1,
$R_1$ is $C_1$-$C_{25}$alkyl, $C_2$-$C_{18}$hydroxyalkyl, $C_2$-$C_{12}$alkyl interrupted by oxygen or by sulfur; $C_3$-$C_{12}$alkenyl, $C_5$-$C_8$cycloalkyl or $C_7$-$C_{12}$phenylalkyl,
when n is 2,
$R_1$ is unsubstituted or $C_1$-$C_4$alkyl-substituted $C_2$-$C_{18}$alkylene, or $C_2$-$C_{18}$alkylene interrupted by oxygen or by sulfur;
$R_2$ is $R_8$—$R_9$—S(O)$_m$—$R_{10}$—,
$R_3$ and $R_4$ are hydrogen, methyl or together are oxygen,
$R_5$ is hydrogen or methyl,
$R_6$ is hydrogen or methyl,
$R_7$ is hydrogen, $C_1$-$C_8$alkyl, O·, hydroxy, —CH$_2$CN, $C_1$-$C_{18}$alkoxy, $C_5$-$C_{12}$cycloalkoxy, $C_3$-$C_6$alkenyl, $C_7$-$C_9$phenylalkyl unsubstituted or substituted on the phenyl by 1, 2 or 3 $C_1$-$C_4$alkyl;

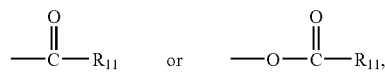

$R_8$ is $C_1$-$C_{18}$alkyl, cyano substituted $C_1$-$C_8$alkyl; or $C_5$-$C_8$cycloalkyl,
$R_9$ is a direct bond or

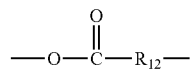

wherein $R_{12}$ is attached to sulfur,
$R_{10}$ is $C_2$-$C_{18}$alkylene, $C_2$-$C_{18}$alkylene interrupted by oxygen or by sulfur; or

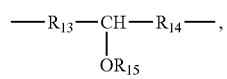

$R_{11}$ is $C_1$-$C_{18}$alkyl, phenyl or $C_3$-$C_{17}$alkenyl,
$R_{12}$ is $C_1$-$C_8$alkylene,
$R_{13}$ is $C_1$-$C_4$alkylene,
$R_{14}$ is $C_1$-$C_4$alkylene,
$R_{15}$ is hydrogen, $C_2$-$C_{18}$alkanoyl or benzoyl,
m is 0, 1 or 2, and
n is 1 or 2.

Alkyl containing up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, iso-octyl, 2-ethylhexyl, 1,1,3-trimethylhexyl, 1,1,3,3-tetramethylpentyl, n-nonyl, tert-nonyl, decyl, undecyl, 1-methylundecyl, n-dodecyl, tert-dodecyl, 1,1,3,3,5,5-hexamethylhexyl, tridecyl, tetradecyl, pentadecyl, hexadecyl, heptadecyl, octadecyl or eicosyl.

Hydroxyalkyl containing from 2 to 18 carbon atoms is a branched or unbranched radical containing preferably from 1 to 3, especially 1 or 2, hydroxy groups, for example hydroxyethyl, 3-hydroxypropyl, 2-hydroxypropyl, 4-hydroxybutyl, 3-hydroxybutyl, 2-hydroxybutyl, 5-hydroxypentyl, 4-hydroxypentyl, 3-hydroxypentyl, 2-hydroxypentyl, 6-hydroxyhexyl, 5-hydroxyhexyl, 4-hydroxyhexyl, 3-hydroxyhexyl, 2-hydroxyhexyl, 7-hydroxyheptyl, 6-hydroxyheptyl, 5-hydroxyheptyl, 4-hydroxyheptyl, 3-hydroxyheptyl, 2-hydroxyheptyl, 8-hydroxyoctyl, 7-hydroxyoctyl, 6-hydroxyoctyl, 5-hydroxyoctyl, 4-hydroxyoctyl, 3-hydroxyoctyl, 2-hydroxyoctyl, 9-hydroxynonyl, 10-hydroxydecyl, 11-hydroxyundecyl, 12-hydroxydodecyl, 13-hydroxytridecyl, 14-hydroxytetradecyl, 15-hydroxypentadecyl, 16-hydroxyhexadecyl, 17-hydroxyheptadecyl, 18-hydroxyoctadecyl or 20-hydroxyeicosyl. A preferred meaning of $R_1$ is $C_2$-$C_{12}$hydroxyalkyl, especially $C_2$-$C_8$hydroxyalkyl, for example hydroxyethyl.

$C_2$-$C_{12}$Alkyl interrupted by oxygen or by sulfur is, for example, $CH_3$—O—$CH_2$—, $CH_3CH_2$—O—$CH_2CH_2$—, $CH_3$—S—$CH_2$—, $CH_3CH_2$—S—$CH_2CH_2$—, $CH_3$—O—$CH_2CH_2$—O—$CH_2$—, $CH_3CH_2$—O—$CH_2CH_2$—O—$CH_2CH_2$—, $CH_3$—(O—$CH_2CH_2$—)$_2$O—$CH_2$—, $CH_3CH_2$—(O—$CH_2CH_2$—)$_2$O—$CH_2CH_2$—, $CH_3$—(O—$CH_2CH_2$—)$_3$O—$CH_2$—, $CH_3$—(O—$CH_2CH_2$—)$_4$O—$CH_2$— or $CH_3CH_2$—(O—$CH_2CH_2$—)$_4$O—$CH_2CH_2$—.

Alkenyl containing from 3 to 12 carbon atoms is a branched or unbranched radical, for example propenyl, 2-butenyl, 3-butenyl, isobutenyl, n-2,4-pentadienyl, 3-methyl-2-butenyl, n-2-octenyl, n-2-dodecenyl or isododecenyl.

$C_5$-$C_8$Cycloalkyl is, for example, cyclopentyl, cyclohexyl, cycloheptyl or cyclooctyl. Preference is given to cyclohexyl.

$C_7$-$C_{12}$Phenylalkyl is, for example, benzyl, α-methylbenzyl, α,α-dimethylbenzyl, 2-phenylethyl, 3-phenylpropyl, 4-phenylbutyl, 5-phenylpentyl or 6-phenylhexyl. Preference is given to benzyl.

Unsubstituted or $C_1$-$C_4$alkyl-substituted $C_1$-$C_{18}$alkylene containing preferably from 1 to 3, especially 1 or 2, branched or unbranched alkyl group radicals, is a branched or unbranched radical, for example methylene, ethylene, propylene, trimethylene, tetramethylene, pentamethylene, hexamethylene, heptamethylene, octamethylene, decamethylene, dodecamethylene or octadecamethylene.

$C_2$-$C_{18}$Alkylene interrupted by oxygen or by sulfur is, for example, —$CH_2$—O—$CH_2$—, —$CH_2CH_2$—O—$CH_2CH_2$—, —$CH_2$—S—$CH_2$—, —$CH_2CH_2$—S—$CH_2CH_2$—, —$CH_2$—O—$CH_2CH_2$—O—$CH_2$—, —$CH_2CH_2$—O—$CH_2CH_2$—O—$CH_2CH_2$—, —$CH_2$—(O—$CH_2CH_2$—)$_2$O—$CH_2$—, —$CH_2CH_2$—(O—$CH_2CH_2$—)$_2$O—$CH_2CH_2$—, —$CH_2$—(O—$CH_2CH_2$—)$_3$O—$CH_2$—, —$CH_2$—(O—$CH_2CH_2$—)$_4$O—$CH_2$— or —$CH_2CH_2$—(O—$CH_2CH_2$—)$_4$O—$CH_2CH_2$—.

Alkoxy containing up to 18 carbon atoms is a branched or unbranched radical, for example methoxy, ethoxy, propoxy, isopropoxy, n-butoxy, isobutoxy, pentyloxy, isopentyloxy, hexyloxy, heptyloxy, octyloxy, decyloxy, tetradecyloxy, hexadecyloxy or octadecyloxy. Preference is given to alkoxy containing from 1 to 12, especially from 1 to 8, for example from 1 to 6, carbon atoms.

$C_5$-$C_{12}$Cycloalkoxy is, for example, cyclopentyloxy, cyclohexyloxy, cycloheptyloxy, cyclooctyloxy, cyclononyloxy, cyclodecyloxy, cycloundecyloxy or cyclododecyloxy. Preference is given to cyclohexyloxy.

Cyano substituted $C_1$-$C_8$alkyl containing from 2 to 18 carbon atom is a branched or unbranched radical containing preferably from 1 to 3, especially 1 or 2, cyano groups, for example cyanoethyl, 3-cyanopropyl, 2-cyanopropyl, 4-cyanobutyl, 3-cyanobutyl, 2-cyanobutyl, 5-cyanopentyl, 4-cyanopentyl, 3-cyanopentyl, 2-cyanopentyl, 6-cyanohexyl, 5-cyanohexyl, 4-cyanohexyl, 3-cyanohexyl, 2-cyanohexyl, 7-cyanoheptyl, 6-cyanoheptyl, 5-cyanoheptyl, 4-cyanoheptyl, 3-cyanoheptyl, 2-cyanoheptyl, 8-cyanooctyl, 7-cyanooctyl, 6-cyanooctyl, 5-cyanooctyl, 4-cyanooctyl, 3-cyanooctyl or 2-cyanooctyl.

Alkanoyl containing from 2 to 18 carbon atoms is a branched or unbranched radical, for example acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl or octadecanoyl.

Of interest are compounds of the formula I, wherein, when n is 1,
$R_1$ is $C_1$-$C_{18}$alkyl, $C_2$-$C_{12}$hydroxyalkyl, $C_4$-$C_8$alkyl interrupted by oxygen or by sulfur; $C_3$-$C_8$alkenyl, $C_5$-$C_7$cycloalkyl or benzyl,
when n is 2,
$R_1$ is unsubstituted or $C_1$-$C_4$alkyl-substituted $C_2$-$C_{12}$alkene, or $C_4$-$C_{12}$alkylene interrupted by oxygen or by sulfur,
$R_2$ is $R_8$—$R_9$—$S(O)_m$—$R_{10}$—,
$R_3$ and $R_4$ are hydrogen or together are oxygen,
$R_5$ and $R_6$ are hydrogen,
$R_7$ is hydrogen, $C_1$-$C_8$alkyl, O·, hydroxy, —$CH_2CN$, $C_1$-$C_{12}$alkoxy, $C_5$-$C_7$cycloalkoxy, $C_3$-$C_8$alkenyl, benzyl,

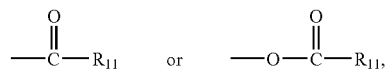

$R_8$ is $C_4$-$C_{18}$alkyl, cyano substituted $C_1$-$C_{18}$alkyl; or $C_5$-$C_7$cycloalkyl,
$R_9$ is a direct bond or

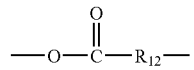

wherein $R_{12}$ is attached to sulfur,
$R_{10}$ is $C_2$-$C_{12}$alkylene, $C_4$-$C_{12}$alkylene interrupted by oxygen or by sulfur; or

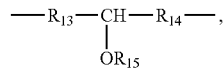

$R_{11}$ is $C_1$-$C_{12}$alkyl, phenyl or $C_3$-$C_{11}$alkenyl,
$R_{12}$ is $C_1$-$C_4$alkylene,
$R_{13}$ is $C_1$-$C_3$alkylene,
$R_{14}$ is $C_1$-$C_3$alkylene,
$R_{15}$ is hydrogen, $C_2$-$C_{12}$alkanoyl or benzoyl,
m is 0, 1 or 2, and
n is 1 or 2.

Preference is given to compounds of the formula I wherein m is 0 or 1.

Preference is given also to compound of the formula I wherein $R_3$, $R_4$, $R_5$ and $R_6$ are hydrogen.

Further preferred compounds of the formula I are those wherein, when n is 1, $R_1$ is $C_2$-$C_{12}$alkyl, $C_2$-$C_8$hydroxyalkyl, $C_4$-$C_8$alkyl interrupted by oxygen; cyclohexyl or benzyl, when n is 2, $R_1$ is $C_3$-$C_8$alkylene, or $C_4$-$C_8$alkylene interrupted by oxygen;

$R_2$ is $R_8$—$R_9$—$S(O)_m$—$R_{10}$—, $R_3$, $R_4$, $R_5$ and $R_6$ are hydrogen, $R_7$ is hydrogen, $C_1$-$C_4$alkyl, $C_1$-$C_8$alkoxy, cyclohexoxy, benzyl,

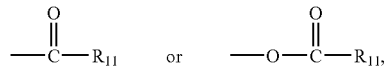

$R_8$ is $C_4$-$C_{14}$alkyl or cyclohexyl, $R_9$ is a direct bond or

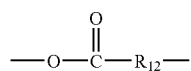

wherein $R_{12}$ is attached to sulfur, $R_{10}$ is $C_2$-$C_8$alkylene, $C_4$-$C_8$alkylene interrupted by oxygen; or

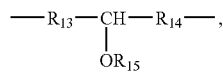

$R_{11}$ is $C_1$-$C_8$alkyl or $C_3$-$C_8$alkenyl, $R_{12}$ is $C_1$-$C_4$alkylene, $R_{13}$ and $R_{14}$ are methylene, $R_{15}$ is hydrogen, $C_2$-$C_4$alkanoyl or benzoyl, m is 0, 1 or 2, and n is 1 or 2.

Particularly interesting compounds of the formula I are those wherein, when n is 1, $R_1$ is $C_3$-$C_5$alkyl, when n is 2, $R_1$ is $C_5$-$C_7$alkylene, $R_2$ is $R_8$—$R_9$—$S(O)_m$—$R_{10}$—, $R_3$, $R_4$, $R_5$ and $R_6$ are hydrogen, $R_7$ is hydrogen or methyl, $R_8$ is $C_6$-$C_{14}$alkyl, $R_9$ is a direct bond or

wherein $R_{12}$ is attached to sulfur, $R_{10}$ is $C_2$-$C_4$alkylene or

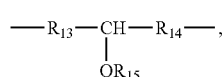

$R_{12}$ is methylene or ethylene, $R_{13}$ and $R_{14}$ are methylene, $R_{15}$ is hydrogen, m is 0, 1 or 2, and n is 1 or 2.

The compounds of the formula I can be prepared in per se known manners. A preferred process for the preparation of the compounds of the formula I comprises the alkylation of the known compounds of the formula Ia

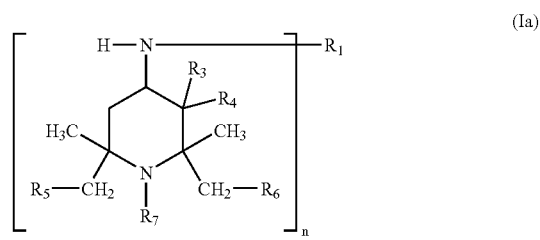

wherein the general symbols are as defined above, with a compound of the formula Ib

wherein $R_8$, $R_9$, $R_{10}$ and m are as defined above, and X is halogen, preferably chlorine, bromine or iodine, in the presence of a base.

The compounds of the formula I are suitable for stabilizing organic materials against oxidative, thermal, dynamic, light-induced and/or ozone-induced degradation. Special attention is drawn to their excellent action as light-stabilizers in the stabilization of organic materials.

Illustrative examples of such materials are:

1. Polymers of mono- and di-olefins, for example polypropylene, polyisobutylene, polybutene-1, poly-4-methylpentene-1, polyvinylcyclohexane, polyisoprene or polybutadiene and also polymerisates of cycloolefins, for example of cyclopentene or norbornene; and also polyethylene (which may optionally be cross-linked), for example high density polyethylene (HDPE), high density polyethylene of high molecular weight (HDPE-HMW), high density polyethylene of ultra-high molecular weight (HDPE-UHMW), medium density polyethylene (MDPE), low density polyethylene (LDPE), and linear low density polyethylene (LLDPE), (VLDPE) and (ULDPE).

Polyolefins, that is to say polymers of monoolefins, as mentioned by way of example in the preceding paragraph, especially polyethylene and polypropylene, can be prepared by various processes, especially by the following methods:

a) by free radical polymerisation (usually at high pressure and high temperature);

b) by means of a catalyst, the catalyst usually containing one or more metals of group IVb, Vb, VIb or VIII. Such metals generally have one or more ligands, such as oxides, halides, alcoholates, esters, ethers, amines, alkyls, alkenyls and/or aryls, which may be either π- or σ-coordinated. Such metal complexes may be free or fixed to carriers, for example to activated magnesium chloride, titanium(III) chloride, aluminium oxide or silicon oxide. Such catalysts may be soluble or insoluble in the polymerisation medium. The catalysts can be active as such in the polymerisation or further activators may be used, for example metal alkyls, metal hydrides, metal alkyl halides, metal alkyl oxides or metal allyl oxanes, the metals being elements of group(s) Ia, IIa and/or IIIa. The activators may be modified, for example, with further ester, ether, amine or silyl ether groups. Such catalyst systems are usually known as Phillips, Standard Oil Indiana, Ziegler (-Natta), TNZ (DuPont), metallocene or Single Site Catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of mono- and di-olefins with one another or with other vinyl monomers, for example ethylene/propylene copolymers, linear low density polyethylene (LLDPE) and mixtures thereof with low density polyethylene (LDPE), propylene/butene-1 copolymers, propylene/isobutylene copolymers, ethylene/butene-1 copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers, for example ethylene/norbornene (COC), ethylene/1-olefin copolymers wherein the 1-olefin is prepared in situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers, ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another and with polymers mentioned under 1), for example polypropylene-ethylene/propylene copolymers, LDPE-ethylene/vinyl acetate copolymers, LDPE-ethylene/acrylic acid copolymers, LLDPE-ethylene/vinyl acetate copolymers, LLDPE-ethylene/acrylic acid copolymers and alternately or randomly structured polyalkylene-carbon monoxide copolymers and mixtures thereof with other polymers, for example polyamides.

4. Hydrocarbon resins (for example $C_5$-$C_9$) including hydrogenated modifications thereof (for example tackifier resins) and mixtures of polyalkylenes and starch.

Homopolymers and copolymers according to 1.) to 4.) can have a syndiotactic, isotactic, semi-isotactic or atactic stereo structure; preference is given to atactic polymers. Stereoblock polymers are also included.

5. Polystyrene, poly(p-methylstyrene), poly($\alpha$-methylstyrene).

6. Aromatic homopolymers and copolymers derived from vinyl-aromatic monomers, for example styrene, $\alpha$-methylstyrene, all isomers of vinyltoluene, for example p-vinyltoluene, all isomers of ethylstyrene, propylstyrene, vinylbiphenyl, vinylnaphthalene, vinylanthracene and mixtures thereof homopolymers and copolymers can have a syndiotactic, isotactic, semi-isotactic or atactic stereo structure; preference is given to atactic polymers. Stereoblock polymers are also included.

6a. Copolymers including the already mentioned vinyl-aromatic monomers and comonomers selected from ethylene, propylene, dienes, nitriles, acids, maleic anhydrides, maleic acid amides, vinyl acetate, vinyl chloride and acrylic acid derivatives and mixtures thereof, for example styrene/butadiene, styrene/acrylonitrile, styrene/ethylene (interpolymers), styrene/alkyl methacrylate, styrene/butadiene/alkyl acrylate and methacrylate, styrene/maleic anhydride, styrene/acrylonitrile/methyl acrylate; high-impact-strength mixtures consisting of styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene or styrene/ethylene-propylene/styrene.

6b. Hydrogenated aromatic polymers prepared by hydrogenation of the polymers mentioned under 6.), especially polycyclohexylethylene (PCHE), often also referred to as polyvinylcyclohexane (PVCH), which is prepared by hydrogenation of atactic polystyrene.

6c. Hydrogenated aromatic polymers prepared by hydrogenation of the polymers mentioned under 6a.).

Homopolymers and copolymers can have a syndiotactic, isotactic, semi-isotactic or atactic stereo structure; preference is given to atactic polymers. Stereoblock polymers are also included.

7. Graft copolymers of vinyl-aromatic monomers, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleic acid imide on polybutadiene; styrene and maleic acid imide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under 6), such as those known, for example, as so-called ABS, MBS, ASA or AES polymers.

8. Halogen-containing polymers, for example polychloroprene, chlorinated rubber, chlorinated and brominated copolymer of isobutylene/isoprene (halobutyl rubber), chlorinated or chlorosulfonated polyethylene, copolymers of ethylene and chlorinated ethylene, epichlorohydrin homo- and co-polymers, especially polymers of halogen-containing vinyl compounds, for example polyvinyl chloride, polyvinylidene chloride, polyvinyl fluoride, polyvinylidene fluoride; and copolymers thereof, such as vinyl chloride/vinylidene chloride, vinyl chloride/vinyl acetate or vinylidene chloride/vinyl acetate.

9. Polymers derived from $\alpha,\beta$-unsaturated acids and derivatives thereof, such as polyacrylates and polymethacrylates, and polymethyl methacrylates, polyacrylamides and polyacrylonitriles impact-resistant-modified with butyl acrylate.

10. Copolymers of the monomers mentioned under 9) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

11. Polymers derived from unsaturated alcohols and amines or their acyl derivatives or acetals, such as polyvinyl alcohol, polyvinyl acetate, stearate, benzoate or maleate, polyvinylbutyral, polyallyl phthalate, polyallylmelamine; and the copolymers thereof with olefins mentioned in Point 1.

12. Homo- and co-polymers of cyclic ethers, such as polyalkylene glycols, polyethylene oxide, polypropylene oxide or copolymers thereof with bisglycidyl ethers.

13. Polyacetals, such as polyoxymethylene, and also those polyoxymethylenes which contain comonomers, for example ethylene oxide; polyacetals that are modified with thermoplastic polyurethanes, acrylates or MBS.

14. Polyphenylene oxides and sulfides and mixtures thereof with styrene polymers or polyamides.

15. Polyurethanes derived from polyethers, polyesters and polybutadienes having terminal hydroxyl groups on the one hand and aliphatic or aromatic polyisocyanates on the other hand, and their initial products.

16. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 12/12, polyamide 11, polyamide 12, aromatic polyamides derived from m-xylene, diamine and adipic acid; polyamides prepared from hexamethylenediamine and iso- and/or tere-phthalic acid and optionally an elastomer as modifier, for example poly-2,4,4-trimethylhexamethylene terephthalamide or poly-m-phenylene isophthalamide; block copolymers of the above-mentioned polyamides with polyolefins, olefin copolymers, ionomers or chemically bonded or grafted elastomers, or with polyethers, for example with polyethylene glycol, polypropylene glycol or polytetramethylene glycol; also polyamides or copolyamides modified with EPDM or ABS; and polyamides condensed during processing ("RIM polyamide systems").

17. Polyureas, polyimides, polyamide imides, polyether imides, polyester imides, polyhydantoins and polybenzimidazoles.

18. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyalkylene naphthalate (PAN) and polyhydroxybenzoates, and also block polyether esters derived from polyethers with hydroxyl terminal groups; and also polyesters modified with polycarbonates or MBS.

19. Polycarbonates and polyester carbonates.

20. Polyketones.

21. Polysulfones, polyether sulfones and polyether ketones.

22. Cross-inked polymers derived from aldehydes on the one hand and phenols, urea or melamine on the other hand, such as phenol-formaldehyde, urea-formaldehyde and melamine-formaldehyde resins.

23. Drying and non-drying alkyd resins.

24. Unsaturated polyester resins derived from copolyesters of saturated and unsaturated dicarboxylic acids with polyhydric alcohols, and also vinyl compounds as cross-linking agents, and also the halogen-containing modifications thereof that are not readily combustible.

25. Cross-linkable acrylic resins derived from substituted acrylic acid esters, e.g. from epoxy acrylates, urethane acrylates or polyester acrylates.

26. Alkyd resins, polyester resins and acrylate resins that are cross-linked with melamine resins, urea resins, isocyanates, isocyanurates, polyisocyanates or epoxy resins.

27. Cross-linked epoxy resins derived from aliphatic, cycloaliphatic, heterocyclic or aromatic glycidyl compounds, e.g. products of diglycidyl ethers of bisphenol A, diglycidyl ethers of bisphenol F, that are cross-linked using customary hardeners, e.g. anhydrides or amines with or without accelerators.

28. Natural polymers such as cellulose, natural rubber, gelatin, and polymer-homologously chemically modified derivatives thereof, such as cellulose acetates, propionates and butyrates, and the cellulose ethers, such as methyl cellulose; and also colophony resins and derivatives.

29. Mixtures (polyblends) of the afore-mentioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

30. Natural and synthetic organic substances that are pure monomeric compounds or mixtures thereof, for example mineral oils, animal or vegetable fats, oils and waxes, or oils, waxes and fats based on synthetic esters (for example phthalates, adipates, phosphates or trimellitates), and admixtures of synthetic esters with mineral oils in any weight ratios, as used, for example, as spin-coating preparations, and aqueous emulsions thereof.

31. Aqueous emulsions of natural or synthetic rubbers, for example natural rubber latex or latexes of carboxylated styrene/butadiene copolymers.

Further objects of the invention are therefore compositions comprising a) an organic material which is susceptible to oxidative, thermal, dynamic, light-induced and/or ozone-induced degradation, and b) at least one compound of the formula I.

Preferred organic materials are natural, semi-synthetic or synthetic polymers, for example polyolefins, styrene copolymers and elastomers.

Especially preferred polyolefins are polyethylene and polypropylene.

Elastomers are to be understood as macromolecular materials that at room temperature after considerable deformation under low stress are capable of returning rapidly to virtually their original shape. See also Hans-Georg Ellias, "An Introduction to Polymer Science", Chapter 12. "Elastomers", pages 388-393, 1997, VCH Verlagsgesellschaft mbH, Weinheim, Germany; or "Ullmann's Encyclopedia of Industrial Chemistry, Fifth, Completely Revised Edition, Volume A 23", pages 221-440 (1993).

The compounds of formula I are added to the organic material to be grafted in an amount of, advantageously, from 0.01 to 10%, for example from 0.1 to 5%, preferably from 0.5 to 3.0%, based on the weight of the organic material to be grafted.

The ungrafted or grafted organic materials may comprise, besides components (a) and (b), further additives, for example the following:

1. Antioxidants 1.1. Alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, linear nonylphenols or nonylphenols branched in the side-chain, e.g. 2,6-dinonyl-4-methylphenol, 2,4-dimethyl-6-(1'-methylundec-1'-yl)-phenol, 2,4-dimethyl-6-(1'-methylheptadec-1'-yl) phenol, 2,4-dimethyl-6-(1'-methyltridec-1'-yl)-phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.6. Alkylidene bisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate],bis(3-tert-butyl-4-hydroxy-5-methylphenyl)dicyclopentadiene, bis[2-3'-tert-butyl-2'-hydroxy-5'-methylbenzyl)-6tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-hydroxy-2-methylphenyl)-4-n-dodecylmercaptobutane, 1,1,5,5-tetra(5-tert-butyl-hydroxy-2-methylphenyl)pentane.

1.7. O—, N— and S-benzyl compounds, for example 3,5,3',5'-tetra-tert-butyl-4,4'-dihydroxy-dibenzyl ether, octadecyl-4-hydroxy-3,5-dimethylbenzyl mercaptoacetate, tridecyl-4-hydroxy-3,5-di-tert-butylbenzyl mercaptoacetate, tris(3,5-di-tert-butyl-4-hydroxybenzyl)amine, bis(4-tert-butyl-3-hydroxy-2,6-dimethylbenzyl) dithioterephthalate, bis(3,5-di-tert-butyl-4-hydroxybenzyl) sulfide, isooctyl-3,5-di-tert-butyl-4-hydroxybenzyl mercaptoacetate.

1.8. Hydroxybenzylated malonates, for example dioctadecyl 2,2-bis(3,5-di-tert-butyl-2-hydroxybenzyl)malonate, dioctadecyl 2-(3-tert-butyl-4-hydroxy-5-methylbenzyl)malonate, didodecylmercaptoethyl 2,2-bis(3,5-di-tert-butyl-4-hydroxybenzyl)malonate, di-[4-(1,1,3,3-tetramethylbutyl)phenyl]2,2-bis(3,5-di-tert-butyl-4-hydroxybenzyl)malonate.

1.9. Hydroxybenzyl aromatic compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetra-methylbenzene, 2,4,6-tris(3,5-di-tert-butyl-4-hydroxybenzyl)phenol.

1.10. Triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl) isocyanurate.

1.11. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, calcium salt of 3,5-di-tert-butyl-4-hydroxybenzyl-phosphonic acid monoethyl ester.

1.12. Acylaminophenols, for example 4-hydroxylauric acid anilide, 4-hydroxystearic acid anilide, N-(3,5-di-tert-butyl-4-hydroxyphenyl)carbamic acid octyl ester.

1.13. Esters of β-(3,5-d)-tert-butyl-4-hydroxyphenyl)propionic acid with mono- or poly-hydric alcohols, for example with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or poly-hydric alcohols, for example with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy)}-1,1-dimethylethyl]-2,4,8,10-tetraoxaspiro[5.5]undecane.

1.15. Esters of β-(3,5-dicyclohexyl-4-hydroxyphenyl)propionic acid with mono- or poly-hydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenylacetic acid with mono- or poly-hydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.17. Amides of β-(3,5-di-tert-butyl-4-hydroxyphenyl) propionic acid, for example N,N'-bis(3,5-di-tert-butyl-4-hydroxyphenylpropionyl)hexamethylenediamine, N,N'-bis(3,5-di-tert-butyl-4-hydroxyphenylpropionyl) trimethylenediamide, N,N'-bis(3,5-di-tert-butyl-4-hydroxyphenylpropionyl)hydrazide), N,N'-bis[2-(3-[3,5-di-tert-butyl-4-hydroxyphenyl]-propionyloxy)ethyl]oxamide (Naugard®XL-1 from Uniroyal).

1.18. Ascorbic Acid (Vitamin C).

1.19. Amine-type antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di(2-naphthyl)-p-phenylenediamine, N-isopropyl-N'-phenyl-p-phenylenediamine, N-(1,3-dimethyl-butyl)-N'-phenyl-p-phenylenediamine, N-1-methylheptyl)-N'-phenyl-p-phenylenediamine, N-cyclohexyl-N'-phenyl-p-phenylenediamines, 4-(p-toluenesulfonamido)-diphenylamine, N,N'-dimethyl-N,N'-di-sebutyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, di(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-di[(2-methylphenyl)amino]ethane, 1,2-di(phenylamino)propane, (o-tolyl)-biguanide, di[4-(1', 3'-dimethylbutyl)phenyl]amine, tert-octylated N-phenyl-1-naphthylamine, mixture of mono- and di-alkylated tert-butyl-/tert-ocyl-diphenylamines, mixture of mono- and di-alkylated nonyldiphenylamines, mixture of mono- and di-alkylated dodecyldiphenylamines, mixture of mono- and di-alkylated isopropyl-/isohexyl-diphenylamines, mixtures of mono- and di-alkylated tert-butyldiphenylamines, 2,3-dihydro-3,3-dimethyl-4H-1,4-benzothiazine, phenothiazine, mixture of mono- and di-alkylated tert-butyl-/tert-ctyl-phenothiazines, mixture of mono- and di-alkylated tert-octylphenothiazines, N-allylphenothiazine or N,N,N',N'-tetraphenyl-1,4-diaminobut-2-ene.

2. UV Absorbers and Light Stabilizers 2.1. 2-(2'-Hydroxyphenyl)-benzotriazoles, for example 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)benzotriazole, 2-(2'-hydroxy-5'-(1,1,3,3-tetramethylbutyl)-phenyl)-benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)-benzotriazole, 2-(2'-hydroxy-4'-octyloxyphenyl)benzotriazole, 2-(3',5'-di-tert-amyl-2'-hydroxyphenyl)-benzotriazole, 2-(3',5'-bis (α,α-dimethylbenzyl)-2'-hydroxyphenyl)-benzotriazole, 2-(3'-tert-butyl-2'-hydroxy-5'-(2-octyloxycarbonylethyl) phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-2-methoxycarbonylethyl)phenyl)-benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy)carbonylethyl]-2'-hydroxyphenyl)-benzotriazole, 2-(3'-dodecyl-2'-hydroxy-5'-methylphenyl)-benzotriazole, 2-(3'-tert-butyl-2'-hydroxy-5'-(2-isooctyloxycarbonylethyl)-phenyl-benzotriazole, 2,2'-methylenebis[4-(1,1,3,3-tetramethylbutyl)-6-benzotriazol-2-yl-phenol]; transesterification product of 2-[3'-tert-butyl-5'-(2-methoxycarbonylethyl)-2'-hydroxyphenyl]-benzotriazole with polyethylene glycol 300;

wherein R=3'-tert-butyl-4'-hydroxy-5'-2H-benzotriazol-2-yl-phenyl; 2-[2'-hydroxy-3'-(α,α-dimethylbenzyl)-5'-(1,1,3, 3-tetramethylbutyl)-phenyl]-benzotriazole; 2-[2'-hydroxy-3'-(1,1,3,3-tetramethylbutyl)-5'-(α,αdimethylbenzyl)-phenyl]-benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy or 2'-hydroxy-4,4'-dimethoxy derivative.

2.3. Esters of unsubstituted or substituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butyl-4-hydroxybenzoic acid octadecyl ester, 3,5-di-tert-butyl-4-hydroxybenzoic acid 2-methyl-4,6-di-tert-butylphenyl ester.

2.4. Acrylates, for example α-cyano-β,β-diphenylacrylic acid ethyl ester or isooctyl ester, α-methoxycarbonylcinnamic acid methyl ester, α-cyano-β-methyl-p-methoxycinnamic acid methyl ester or butyl ester, α-methoxycarbonyl-p-methoxycinnamic acid methyl ester, N-(β-methoxycarbonyl-β-cyanovinyl)-2-methyl-indoline.

2.5. Nickel compounds, for example nickel complexes of 2,2'-thio-bis[4-(1,3,3-tetra-methylbutyl)phenol], such as the 1:1 or 1:2 complex, optionally with additional ligands, such as n-butylamine, triethanolamine or N-cyclohexyldiethanolamine, nickel dibutyl dithiocarbamate, nickel salts of 4-hydroxy-3,5-di-tert-butylbenzylphosphonic acid monoalkyl esters, such as of the methyl or ethyl ester, nickel complexes of ketoximes, such as of 2-hydroxy-4-methylphenylundecyl ketoxime, nickel complexes of 1-phenyl-4-lauroyl-5-hydroxypyrazole, optionally with additional ligands.

2.6. Sterically hindered amines, for example bis(2,2,6,6-tetramethylpiperid-4-yl) sebacate, bis(2,2,6,6-tetramethylpiperid-4-yl) succinate, bis(1,2,2,6,6-pentamethylpiperid-4-yl) sebacate, bis(1-octyloxy-2,2,6,6-tetramethylpiperid-4-yl) sebacate, n-butyl-3,5-di-tert-butyl-4-hydroxybenzylmalonic acid bis(1,2,2,6,6-pentamethylpiperidyl) ester, condensation product of 1-hydroxyethyl-2,2,6,6-tetramethyl-4-hydroxypiperidine and succinic acid, linear or cyclic condensation products of N,N'-bis(2,2,6,6-tetramethyl-4-piperidyl)hexamethylenediamine and 4-tert-octylamino-2,6-dichloro-1,3, 5-s-triazine, tris(2,2,6,6-tetramethyl-4-piperidyl) nitrilotriacetate, tetrakis(2,2,6,6-tetramethyl 4-piperidyl)-1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, linear or cyclic condensation products of N,N'-bis(2, 2,6,6-tetramethyl-4-piperidyl)hexamethylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-aminopropylamino)ethane, condensation product of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, mixture of 4-hexadecyloxy- and 4-stearyloxy-2,2,6,6-tetramethylpiperidine, condensation product of N,N'-bis(2,2,6,6-tetramethyl-4-piperidyl) hexamethylenediamine and 4-cyclohexylamino-2,6-dichloro-1,3,5-triazine, condensation product of 1,2-bis(3-aminopropylamino)ethane and 2,4,6-trichloro-1,3,5-triazine and 4-butylamino-2,2,6,6-tetramethylpiperidine (CAS Reg. No. [136504-96-6]); condensation product of 1,6-diaminohexane and 2,4,6-trichloro-1,3,5-triazine and also N,N-dibutylamine and 4-butylamino-2,2,6,6-tetramethylpiperidine (CAS Reg. No. [19226847]); N-(2,2,6,6-tetramethyl-4-piperidyl)-n-dodecylsuccinimide, N-(1,2,2,6,6-pentamethyl-6-piperidyl)-n-dodecylsuccinimide, 2-undecyl-7,7,9,9-tetramethyl-1-oxa-3,8-diaza-4-oxo-spiro[4.5]decane, reaction product of 7,7,9,9-tetramethyl-2-cycloundecyl-1-oxa-3,8-diaza-4-oxo-spiro[4.5]decane and epichlorohydrin, 1,1-bis (1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, diester of 4-methoxymethylenemalonic acid with 1,2,2,6,6-pentamethyl-4hydroxypiperidine, poly[methylpropyloxy-3-oxy-4-(2,2,6,6-tetramethyl-4-piperidyl)]siloxane, reaction product of maleic anhydride α-olefin copolymer and 2,2,6,6-tetramethyl-4-aminopiperidine or 1,2,2,6,6-pentamethyl-4-aminopiperidine.

2.7. Oxalic acid diamides, for example 4,4'-dioctyloxy oxanilide, 2,2'-diethoxy oxanilide, 2,2'-dioctyloxy-5,5'-di-tert-butyl oxanilide, 2,2'-didodecyloxy-5,5'-di-tert-butyl oxanilide, 2-ethoxy-2'-ethyl oxanilide, N,N'-bis(3-dimethylaminopropyl) oxalamide, 2-ethoxy-5-tert-butyl-2-ethyl oxanilide and a mixture thereof with 2-ethoxy-2'-ethyl-5,4'-di-tert-butyl oxanilide, mixtures of o- and p-methoxy- and also of o- and p-ethoxy-di-substituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxalic acid diamide, N-salicylal-N'-salicyloylhydrazine, N,N'-bis (salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic acid dihydrazide, oxanilide, isophthalic acid dihydrazide, sebacic acid bis-phenylhydrazide, N,N'-diacetyladipic acid dihydrazide, N,N'-bis-salicyloyloxalic acid dihydrazide, N,N'-bis-salicyloylthiopropionic acid dihydrazide.

4. Phosphites and phosphonites, e.g. triphenyl phosphite, diphenylalkyl phosphites, phenyldialkyl phosphites, tris (nonylphenyl)phosphite, trilauryl phosphite, trioctadecyl phosphite, distearyl-pentaerythritol diphosphite, tris(2,4-di-tert-butylphenyl)phosphite, diisodecylpentaerythritol diphosphite, bis(2,4-di-tert-butylphenyl)pentaerythritol diphosphite, bis(2,4-di-cumylphenyl)-pentaerythritol diphosphite, bis(2,6-di-tert-butyl-4-methylphenyl)pentaerythritol diphosphite, bis-isodecyloxy-pentaerythritol diphosphite, bis(2,4-di-tert-butyl-6-methylphenyl)pentaerythritol diphosphite, bis(2,4,6-tri-tert-butylphenyl)pentaerythritol diphosphite, tristearyl sorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, bis(2,4-di-tert-butyl-6-methylphenyl)methylphosphite, bis(2,4-di-tert-butyl-6-methylphenyl) ethylphosphite, 6-fluoro-2,4,8,10-tetra-tert-butyl-12-methyl-dibenzo[d,g]-1,3,2-dioxaphosphocine, 2,2',2''-nitrilo[triethyl-tris(3,3',5,5'-tetra-tert-butyl-1,1'-biphenyl-2,2'-diyl)-phosphite], 2-ethylhexyl-(3,3',5,5'-tetra-tert-butyl-1,1'-biphenyl-2,2'-diyl) phosphite, 5-butyl-5-ethyl-2-(2,4,6-tri-tert-butylphenoxy)-1,3,2-dioxaphosphirane.

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadeylhydroxylamine, N-heptadecyl-N-octadecylhydroxylamine, N,N-dialkylhydroxylamine from hydrogenated tallow fatty amines.

6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-octadecyl-alpha-pentadecylnitrone, N-heptadecyl-alpha-heptadecylnitrone, N-octadecyl-alpha-hexadecylnitrone, nitrones derived from N,N-dialkyl-hydroxylamines prepared from hydrogenated tallow fatty amines.

7. Thiosynergistic compounds, for example thiodipropionic acid dilauryl ester or thiodipropionic acid distearyl ester.

8. Peroxide-destroying compounds, for example esters of β-thio-dipropionic acid, for example the lauryl, stearyl, myristyl or tridecyl ester, mercaptobenzimidazole, the zinc salt of 2-mercaptobenzimidazole, zinc dibutyldithiocarbamate, dioctadecyldisulfide, pentaerythritol tetrakis(β-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal and alkaline earth metal salts of higher fatty acids, for example calcium stearate, zinc stearate, magnesium behenate, magnesium stearate, sodium ricinoleate, potassium palmitate, antimony pyrocatecholate or zinc pyrocatecholate.

11. Nucleating agents, for example inorganic substances, e.g. talc, metal oxides, such as titanium dioxide or magnesium oxide, phosphates, carbonates or sulfates of preferably alkaline earth metals; organic compounds, such as mono- or poly-carboxylic acids and their salts, e.g. 4-tert-butylbenzoic acid, adipic acid, diphenylacetic acid, sodium succinate or sodium benzoate; polymeric compounds, for example ionic copolymerisates ("ionomers"). Special preference is given to 1,3:2,4-bis(3',4'-dimethylbenzylidene)sorbitol, 1,3:2,4-di (paramethyldibenzylidene)sorbitol and 1,3:2,4-di(benzylidene)sorbitol.

12. Fillers and reinforcing agents, for example calcium carbonate, silicates, glass fibres, glass beads, talc, kaolin, mica, barium sulfate, metal oxides and hydroxides, carbon black, graphite, wood powders, and powders and fibres of other natural products, synthetic fibres.

13. Other additives, for example plasticisers, lubricants, emulsifiers, pigments, rheology additives, catalysts, flow improvers, optical brighteners, flame retardants, antistatics, blowing agents.

14. Benzofuranones and indolinones, for example as described in U.S. Pat. No. 4,325,863; U.S. Pat. No. 4,338,244; U.S. Pat. No. 5,175,312, U.S. Pat. No. 5,216,052; U.S. Pat. No. 5,252,643; DE-A-4 316 611; DE-A-4 316 622; DE-A-4 316 876; EP-A-0 589 839 or EP-A-0 591 102, or 3-[4-(2-acetoxyethoxy)phenyl]-5,7-di-tert-butyl-benzofuran-2-one, 5,7-di-tert-butyl-3-[4-(2-stearoyloxyethoxy)phenyl]

benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxy-phenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The present invention accordingly relates also to compositions comprising a) an organic material which is susceptible to oxidative, thermal, dynamic, light-induced and/for ozone-induced degradation, b) at least one compound of the formula I, and c), as further additive, at least one compound selected from the group consisting of phenolic antioxidants, light-stabilizers, amine-type antioxidants, processing stabilizers, solvents, pigments, dyes, fillers, flow improvers, dispersing agents, plasticizers, vulcanisation activators, vulcanisation accelerators, vulcanisation agents, charge control agents, compatibilizers, adhesion promoters, toughening agents, thixotropic agents, levelling assistants and/or metal passivators.

Preferred additives in the compositions according to the invention are, for example, antioxidants, e.g. phenolic antioxidants (points 1.1 to 1.17 of the list) or amine-type antioxidants (point 1.19 of the list), organic phosphonites or phosphonites (point 4 of the list) and/or thio-synergistic compounds (point 7 of the list).

The additional additives are added, for example, in concentrations of from 0.01 to 10%, based on the total weight of the organic material.

The grafting of the organic materials and also, where applicable, the incorporation of further additives into the organic materials are carried out according to known methods, for example during mixing in internal (Banbury) mixers, on mixing roll mills or in mixing extruders, before or during shaping or vulcanisation (in the case of elastomers) or also by application of the dissolved or dispersed compounds of the formula I to the polymers, where appropriate with subsequent evaporation of the solvent. The compounds of the formula I and, where applicable, further additives can also be added, to the polymer being grafted, in the form of a masterbatch containing them in a concentration of, for example, from 2.5 to 25% by weight The compounds of the formula I and, where applicable, further additives can also be added before or during the polymerisation of polymers. In the case of crude rubber, the compounds of the formula I, together with further components, for example carbon black as filler and/or extender oils, can be added during cross-linking.

The compounds of the formula I are chemically bonded (grafted) to polymer chains under processing conditions (mixing, vulcanisation etc.). The compounds of the formula I are stable to extraction, that is to say they still possess good protective action after the substrate has been exposed to intensive extraction. The loss of compounds of the formula I caused by migration or extraction from the polymers is extremely small.

The elastomers grafted with the compounds of the formula I furthermore exhibit markedly improved, desirable gloss formation, which means that the surface gloss of the elastomer grafted in accordance with the invention is significantly greater, after exposure to the action of ozone, than that of a non-stabilized elastomer or of an elastomer stabilized in accordance with the prior art.

The compounds of the formula I and, where applicable, further additives can be incorporated into the polymer being grafted in pure form or encapsulated in waxes, oils or polymers.

The compounds of the formula I and, where applicable, further additives can also be sprayed onto the polymer being grafted. They are capable of diluting other additives (for example the customary additives mentioned hereinbefore) or melts thereof, so that they can also be sprayed together with those additives onto the polymer being grafted.

The polymers grafted in that manner can be used in a very wide variety of forms, for example as small bands, moulding materials, profiles, conveyor belts or tyres.

The invention relates also to compositions comprising a functional fluid, preferably from the series of lubricants, hydraulic fluids and metal-working fluids and also fuels for powering engines of the 4-stroke, Otto, 2-stroke, diesel, Wankel and orbital types, and at least one compound of the formula I.

The compounds of the formula I may preferably be used in lubricants and fuels as multifunctional stabilizers, that is to say they combine in themselves antioxidative, friction-reducing, extreme-pressure-protection and wear-protection action and also anti-corrosion properties.

Preferred lubricants and fuels and related products are engine oils, turbine oils, gear oils, hydraulic fluids, diesel or Otto fuels, metal-working fluids and lubricating greases.

Especially preferred lubricants are mineral oils, synthetic oils or mixtures thereof.

Products known per se are used as functional fluids from the series of lubricants, hydraulic fluids and metalworking fluids.

The lubricants and hydraulic fluids that come into consideration will be familiar to the person skilled in the art and are described in the relevant specialist literature, such as, for example, in Dieter Klamann, "Schmierstoffe und verwandte Produkte" [Lubricants and related products] (Verlag Chemie, Weinheim, 1982), in Schewe-Kobek "Das Schmiermittel-Taschenbuch" [The lubricant handbook] (Dr. Alfred Hüthig-Veriag, Heidelberg, 1974) and in "Ullmanns Enzyklopädie der technischen Chemie" [Ullmann's Encyclopaedia of Industrial Chemistry], Vol. 13, pages 85-94 (Verlag Chemie, Weinheim, 1977).

The lubricants are especially oils and greases, for example based on a mineral oil. Oils are preferred.

A further group of lubricants that may be used are vegetable or animal oils, greases, tallows and waxes or mixtures thereof with one another or mixtures with the mentioned mineral or synthetic oils.

Vegetable and animal oils, greases, tallows and waxes are, for example, palm-kernel oil, palm oil, olive oil, rapeseed oil, rape oil, linseed oil, groundnut oil, soybean oil, cottonseed oil, sunflower oil, pumpkin seed oil, coconut oil, maize oil, castor oil, tree nut oil and mixtures thereof, fish oils, tallows obtained from slaughtered animals, such as beef tallow, neatsfoot oil and bone oil, and modified, epoxidised and sulfoxidised forms thereof, for example epoxidised soybean oil.

The mineral oils are based especially on hydrocarbon compounds.

Examples of synthetic lubricants include lubricants based on aliphatic or aromatic carboxy esters, polymeric esters, polyalkylene oxides, phosphoric acid esters, poly-alpha-olefins or silicones, a diester of a divalent acid with a monohydric alcohol, such as, for example, dioctyl sebacate or dinonyl adipate, a triester of trimethylolpropane with a monovalent acid or with a mixture of such acids, such as, for example, trimethylolpropane tripelargonate, trimethylolpropane tricaprylate or mixtures thereof, a tetraester of pentaerythritol with a monovalent acid or with a mixture of such acids, such as, for example, pentaerythritol tetracaprylate, or a complex ester of monovalent and divalent acids with polyhydric alcohols, for example a complex ester of trimethylolpropane with caprylic and sebacic add, or a mixture thereof. Apart from mineral oils there are especially suitable, for example, poly-alpha-olefins, ester-based lubricants, phosphates, glycols, polyglycols and polyalkylene glycols, and also mixtures thereof with water.

Metal-working fluids and hydraulic fluids may be prepared on the basis of the same substances as those described above for the lubricants, such fluids frequently being emulsions of such substances in water or other liquids.

Lubricant and fuel compositions according to the invention are used, for example, in internal combustion engines, e.g. In motorised vehicles equipped with, for example, engines of the Otto, diesel, two-stroke, Wankel or orbital type.

The compounds of the formula I are readily soluble in lubricants and fuels, metal-working fluids and hydraulic fluids and are therefore especially suitable as additives for lubricants and fuels, metal-working fluids and hydraulic fluids.

As additives in lubricants, the compounds of the formula I are effective even in very small amounts. They are mixed in with the lubricants advantageously in an amount of from 0.01 to 5% by weight, preferably in an amount of from 0.05 to 3% by weight and very especially in an amount of from 0.1 to 2% by weight, in each case based on the lubricant.

The compounds of the formula I may be mixed in with the lubricants and fuels in a manner known per se. The compounds of the formula I are readily soluble, for example, in oils. It is also possible to prepare a so-called master batch, which may be diluted, as a function of use, with the appropriate lubricant or fuel to the concentrations suitable for use. In such cases concentrations above 1% by weight are possible.

The lubricants and fuels, metalworking fluids and hydraulic fluids may additionally comprise other additives that are added in order to improve their basic properties still further; such additives include: further antioxidants, metal passivators, rust inhibitors, viscosity index improvers, pour-point depressants, dispersants, detergents, coefficient of friction reducers, further extreme-pressure additives and anti-wear additives. Such further additives are added advantageously in an amount of from 0.01 to 5% by weight.

A number of such compounds can be found, for example, in the above list "1. Antioxidants", especially points 1.1 to 1.19. In addition, further additives may be mentioned by way of example:

Examples of Further Antioxidants:

Aliphatic or aromatic phosphites, esters of thiodipropionic acid or thiodiacetic acid or salts of dithiocarbamic or dithiophosphoric acid, 2,2,12,12-tetramethyl-5,9-dihydroxy-3,7,11-trithiatridecane and 2,2,15,15-tetramethyl-5,12-dihydroxy-3,7,10,14-tetrathiahexadecane.

Examples of Metal Deactivators, e.g. for Copper, are:
a) Benzotriazoles and derivatives thereof, e.g. 2-mercaptobenzotriazole, 2,5-dimercaptobenzotriazole, 4- or 5-alkylbenzotriazoles (e.g. tolutriazole) and derivatives thereof, 4,5,6,7-tetrahydrobenzotriazole, 5,5'-methylenebis-benzotriazole; Mannich bases of benzotriazole or tolutriazole, such as 1-[di(2-ethylhexyl)aminomethyl]tolutriazole and 1-[di(2-ethylhexyl)aminomethyl]benzotriazole; alkoxyalkylbenzotriazoles, such as 1-nonyloxymethyl)benzotriazole, 1-(1-butoxyethyl)benzotriazole and 1-(1-cyclohexyloxybutyl)tolutriazole.
b) 1,2,4-Triazoles and derivatives thereof, e.g. 3-alkyl- (or -aryl-)1,2,4-triazoles, Mannich bases of 1,2,4-triazoles, such as 1-[di(2-ethylhexyl)aminomethyl]-1,2,4-triazole; alkoxyalkyl-1,2,4-triazoles, such as 1-(1-butoxyethyl)-1,2,4-triazole; acylated 3-amino-1,2,4-triazoles.
c) Imidazole derivatives, e.g. 4,4'-methylenebis(2-undecyl-5-methyl)imidazole and bis[(N-methyl)imidazol-2-yl] carbinol-octyl ether.
d) Sulfur-containing heterocyclic compounds, e.g. 2-mercaptobenzothiazole, 2,5-dimercapto-1,3,4-thiadiazole, 2,5-dimercaptobenzothiadiazole and derivatives thereof; 3,5-bis[di(2-ethylhexyl)aminomethyl]-1,3,4-thiadiazolin-2-one.
e) Amino compounds, e.g. salicylidene-propylenediamine, salicylaminoguanidine and salts thereof.

Examples of Rust Inhibitors are:
a) Organic adds, their esters, metal salts, amine salts and anhydrides, e.g. alkyl- and alkenyl-succinic acids and their partial esters with alcohols, diols or hydroxycarboxylic acids, partial amides of alkyl- and alkenyl-succinic acids, 4-nonylphenoxyacetic acid, alkoxy- and alkoxyethoxycarboxylic acids, such as dodecyloxyacetic acid, dodecyloxy-(ethoxy)acetic acid and amine salts thereof, and also N-oleoyl-sarcosine, sorbitan monooleate, lead naphthenate, alkenylsuccinic acid anhydrides, e.g. dodecenylsuccinic acid anhydride, 2-(2-carboxyethyl)-1-dodecyl-3-methylglycerol and salts thereof, especially sodium and triethanolamine salts thereof.
b) Nitrogen-containing compounds, e.g.:
   i. Primary, secondary or tertiary, aliphatic or cycloallphatic amines and amine salts of organic and inorganic acids, e.g. oil-soluble alkylammonium carboxylates, and 1-[N,N-bis(2-hydroxyethyl)amino]-3-(4-nonylphenoxy)propan-2-ol.
   ii. Heterocylic compounds, e.g.: substituted imidazolines and oxazolines, e.g. 2-heptadecenyl-1-(2-hydroxyethyl) imidazoline.
c) Phosphorus containing compounds, e.g.:
   Amine salts of phosphoric acid partial esters or phosphonic acid partial esters, zinc dialkyldithiophosphates.
d) Sulfur-containing compounds, e.g.:
   Barium dinonylnaphthalene sulfonates, calcium petroleum sulfonates, alkylthio-substituted aliphatic carboxylic acids, esters of aliphatic 2-sulfocarboxylic acids and salts thereof.
e) Glycerol derivatives, e.g.:
   Glycerol monooleate, 1-(alkylphenoxy)-3-(2-hydroxyethyl)glycerols, 1-(alkylphenoxy)-3-(2,3-dihydroxypropyl)glycerols, 2-carboxyalkyl-1,3-dialkylglycerols.

Examples of Viscosity Index Improvers are:
Polyacrylates, polymethacrylates, vinylpyrrolidone/methacrylate copolymers, polyvinylpyrrolidones, polybutenes, olefin copolymers, styrene/acrylate copolymers, polyethers.

Examples of Pour-point Depressants are:
Poly(meth)acrylates, ethylene/vinyl acetate copolymer, alkylpolystyrenes, fumarate copolymers, alkylated naphthalene derivatives.

Examples of Dispersants/Surfactants are:
Polybutenylsuccinic acid amides or imides, polybutenylphosphonic acid derivatives, basic magnesium, calcium and barium sulfonates and phenolates.

Examples of Extreme-pressure and Anti-wear Additives are:

Sulfur- and/or phosphorus- and/or halogen-containing compounds, such as, for example, chlorinated paraffins, sulfurated olefins or vegetable oils (soybean/rape oil), alkyl- or aryl-di- or -tri-sulfides, zinc dialkyldithiophosphates, zinc dithiocarbamates such as zinc diamyldithiocarbamate, molybdenum dithioates such as molybdenum dithiocarbamates, triaryl phosphates such as tritolyl phosphate, tricresyl phosphate, phenyl phosphate isopropyl ester, amine salts of mono- or di-alkylphosphoric acids such as the amine salts of mono-/di-hexyl phosphate, amine salts of alkylphosphonic acids such as the amine salt of methylphosphonic acid, triaryl phosphites such as tris[nonylphenyl] phosphate, dialkyl phosphites such as dioctyl phosphite, triaryl monothiophosphates such as triphenyl thionophosphate or tris[isononylpheny] thionophosphate or tert-butylated triphenyl thionophosphate, substituted trialkyl mono- or di-thiophosphates such as diisopropoxyphosphinothioyl)thio]propionate or butylene-1,3-bis[(diisobutoxyphosphinothioyl)propionate, trithiophosphates such as trithiophosphoric acid S,S,S-tris(isooctyl-2-acetates), amine salts of 3-hydroxy-1,3-thiaphosphetane-3-oxide, benzotriazoles or derivatives thereof such as bis(2-ethylhexyl)aminomethyltolutriazole, dithiocarbamates such as methylene-bis-dibutyldithiocarbamate, derivatives of 2-mercaptobenzothiazole such as 1-[N,N-bis(2-ethylhexyl)aminomethyl]-2-mercapto-1H-1,3-benzothiazole, derivatives of 2,5-dimercapto-1,3,4-thiadiazole such as 2,5-bis(tert-nonyldithio)-1,3,4-thiadiazole.

Examples of Coefficient of Friction Reducers are:

Lard oil, oleic acid, tallow, rape oil, sulfurated fats, amines. Further examples are given in EP-A-0 565 487.

Examples of Special Additives for use in Water/Oil Metalworking Fluids and Hydraulic Fluids are:

Emulsifers: petroleum sulfonates, amines, such as polyoxyethylated fatty amines, non-ionic surface-active substances;

buffers: alkanolamines;

biocides: triazines, thiazolinones, tris-nitromethane, morpholine, sodium pyridenethol;

speed improvers: calcium and barium sulfonates;

Examples of Fuel Additives:

Fuel additives are described in Kirk-Othmer, Encyclopedia of Chemical Technology, Vol 12, 1994 and in this instance are essentially petrol and diesel additives:

Petrol: dyes, especially azo dyes;

Antioxidants: aminic, especially para-phenylenediamines, or phenolic, e.g. 2,6-di-tert-butylphenol, as described above;

Metal deactivators: especially N,N'-disallcylidene-1,2-propane, benzotriazole, EDTA;

Rust inhibitors: for example carboxylic acids, sulfonates, amines or amine salts;

Dispersants: e.g. esters, high-molecular-weight amines, Mannich bases, succinimides, borated succinimides;

Detergents: for example fatty acid amides, nonpolymeric amines, polybutene succinimides, polyether amines, low-molecular-weight amines, sulfonates, salicylic acid derivatives;

Demulsifiers: for example long-chain alcohols or phenols containing polyethylene or -butylene groups;

Antiknock agents: tetralkyl lead, manganese methylcyclopentadienyltricarbonyl;

Oxygen compounds: esters of vegetable oils, ethers, alcohols for improving burn behaviour, Diesel: ignition improvers (cetane improvers), e.g. alkyl nitrates, ether nitrates, alkyl diglycol nitrates, organic peroxides;

Stabilizers for, especially, cracked diesel: amines and other N-containing compounds that act as radical traps.

Especially preferred further additives in lubricants are aminic antioxidants, especially mixtures of mono- and di-alkylated tert-butyl-/tert-octyl-phenylamines.

The present invention relates also to the use of the components of the formula I for stabilizing organic materials, especially as additives in lubricants and fuels, hydraulic fluids or metal-working fluids, preferably in hydraulic oils and gear oils. The use according to the invention includes protection of the metal components to be lubricated against mechanical attrition (wear protection) and corrosion protection activity and also antioxidation activity—with respect both to the lubricant and to the metal components.

The present invention relates also to a method of stabilizing an organic material against oxidative, thermal, dynamic, light-induced and/or ozone-induced degradation, which comprises incorporating therein, applying thereto or grafting the organic material with at least one compound of the formula I.

The present invention relates also to a method of grafting compounds of the formula I onto an organic material, which comprises heating, in a processing apparatus for organic materials, a mixture of an organic material and at least one compound of the formula I above the softening point of the organic material and allowing them to react with one another.

A further embodiment of the present invention is the use of compounds of the formula I as stabilizers for organic materials against oxidative, thermal, dynamic, light-induced and/or ozone-induced degradation.

A further embodiment of the present invention is the use of compounds of the formula I as grafting agents for organic materials.

Preferred compounds of the formula I for the above-mentioned methods and uses are the same as the preferences expressed hereinbefore for the novel compounds of the formula I.

The following Examples further illustrate the invention. Parts or percentages relate to weight.

EXAMPLE 1

Preparation of Compounds 100, 101, 102 and 103
(Table 1)

A solution of 1 mol of 4-butylamino-2,2,6,6-tetramethylpiperidine, 1.05 mol of 1-(3-chloropropylthio)-n-dodecane [Cl(CH$_2$)$_3$S-n-C$_{12}$H$_{25}$] and 1.30 mol of potassium carbonate in 420 ml of dimethylformamide is heated at 100° C. for 20 hours. The reaction mixture is quenched with ice water and extracted with ethyl acetate. Evaporation of the solvent and short path distillation of the residue leads to compound 100 (yield 73%), b.p. 185-190° C. at 0.02 bar, yellowish wax, MS(EI): 454 (M$^+$).

Compounds 101, 102 and 103 are obtained in analogy to Example 1 using 1-(3-chloropropylthio)-tert-dodecane [Cl(CH$_2$)$_3$S-tert-C$_{12}$H$_{25}$], Cl(CH$_2$)$_3$—S—CH$_2$—CH$_2$CO$_2$iso-octyl and Cl(CH$_2$)$_3$—S—CH$_2$CO$_2$iso-octyl instead of 1-(3-chloropropylthio)-n-dodecane. Compound 101: yield 68%, b.p. 195-200° C. at 0.02 mbar, yellowish oil, MS(EI): 454 (M$^+$). Compound 102: yield 73%, b.p. 170° C. at 0.03 mbar, yellowish oil, MS(EI): 470 (M$^+$). Compound 103: yield 95%, b.p. 175-180° C. at 0.02 mbar, orange oil, MS(EI): 456 (M$^+$).

EXAMPLE 2

Preparation of Compounds 104, 105 and 106 (Table 1)

A mixture of 1 mol of 4-butylamino-2,2,6,6-tetramethylpiperidine and 1.1 mol of glycidyl n-dodecyl thioether is heated at 110° C. for 25 hours. Short path distillation leads to compound 104 (yield 69%), b.p. 185-190° C. at 0.02 bar, yellowish oil, MS(EI): 471 (M⁺).

Compounds 105 and 106 are obtained in analogy to Example 2 using glycidyl tert-dodecyl thioether and glycidyl 2-(iso-octyloxycarbonyl)ethyl thioether

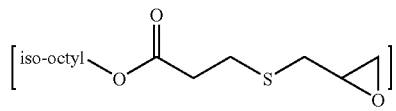

instead of glycidyl n-dodecyl thioether. Compound 105: yield 78%, b.p. 185° C. at 0.05 mbar, yellowish oil, MS(EI): 471 (M⁺). Compound 106: yield 80%, b.p. 140° C. at 0.02 mbar, brownish oil, MS(CI): 487 (MH⁺).

EXAMPLE 3

Preparation of Compounds 107-112 (Table 1)

A mixture of 1 mol of compound 100 [prepared according to Example 1], 1.13 mol of formaldehyde and 1.10 mol of formic acid in 1200 ml of water and 1300 ml of xylene is heated at 70° C. for 20 hours. The reaction mixture is quenched with aqueous sodium hydroxide solution and extracted with ethyl acetate. Evaporation of the solvent and short path distillation of the residue leads to compound 107 (yield 93%), b.p. 185-190° C. at 0.02 bar, yellowish wax, MS(EI): 468 (M⁺).

Compounds 108-112 are obtained in analogy to Example 3 using compounds 101-105 [prepared according to Examples 1 and 2] instead of compound 100. Compound 108: yield 81%, yellowish oil, MS(CI): 469 (MH⁺). Compound 109: yield 94%, yellowish oil, MS(CI): 485 (MH⁺). Compound 110: yield 96%, yellowish oil, MS(CI): 471 (MH⁺). Compound 111: yield 96%, yellowish oil, MS (CI): 485 (MH⁺). Compound 112: yield 93%, yellow oil, MS (CI): 485 (MH⁺).

EXAMPLE 4

Preparation of Compounds 117, 118, 121 and 124 (Table 1)

A solution of 1 mol of compound 104 [prepared according to Example 2], 1.5 mal of 35% aequeous hydrogen peroxide in acetone is stirred at 40-45° C. for 20 hours. The reaction mixture is diluted with water, the acetone distilled off and the aqueous phase extracted three times with methylene chloride. The organic phases are combined, dried over sodium sulfate and concentrated using a vacuum rotary evaporator. The residue yields 91% of compound 117 (Table 1), yellow oil, MS (APCI): 486 (M⁺).

Compounds 118, 121 and 124 are obtained in analogy to Example 4 using compounds 105, [prepared according to Example 2], 112 [prepared according to Example 3] and 111 [prepared according to Example 3] instead of compound 104. Compound 118: yield 81%, orange resin, MS(APCI): 486 (M⁺). Compound 121: yield 28%, yellowish oil, MS(APCI): 484 (M⁺). Compound 124: yield 46%, yellowish oil, MS(APCI): 500 (M⁺).

EXAMPLE 5

Preparation of Compounds 113-116, 119, 120, 122, 123 and 125 (Table 1)

A solution of 1 mmol of compound 100 [prepared according to Example 1], 1.5 mol of hydrogen peroxide/urea tablet [30% hydrogen peroxide] in 10 ml ethanol is stirred at 40° C. for 20 hours. The reaction mixture Is diluted with water, the ethanol distilled off and the aqueous phase extracted three times with methylene chloride. The organic phases are combined, dried over sodium sulfate and concentrated using a vacuum rotary evaporator. The residue yields 93% of compound 113 (Table 1), yellowish oil, MS (APCI): 470 (M⁺).

Compounds 114, 115, 116, 119, 120, 122, 123 and 125 are obtained in analogy to Example 5 using compounds 101, 102, 103 [all prepared according to Example 1], 106 [prepared according to Example 2], 107, 109, 110 and 112 [all prepared according to Example 3].

Compound 114: yield 90%, yellowish oil, MS(APCI): 470 (M⁺). Compound 115: yield 76%, yellowish oil, MS(APCI): 486 (M⁺). Compound 116: yield 64%, orange oil, MS(APCI): 472 (M⁺). Compound 119: yield 59%, brownish oil, MS(APCI): 502 (M⁺). Compound 120: yield 85%, yellowish oil. MS(APCI): 484 (M⁺). Compound 122: yield 76%, yellowish oil, MS(APCI): 500 (M⁺). Compound 123: yield 64%, yellowish oil, MS(APCI): 486 (M⁺). Compound 125: yield 93%, yellowish resin, MS(APCI): 500 (M⁺).

EXAMPLE 6

Preparation of Compounds 126-135 (Table 1)

Compounds 126-135 (Table 1) are obtained in analogy to the former Examples 1-5 from the corresponding starting materials. The oxidations are carried out in analogy to Example 5 or with hydrogen peroxide in acetic acid or formic acid or formic acid/Water at 0-25° C. (compounds 127, 128, 131 and 134). Compound 126: MS (APCI): 878 (M⁺). Compound 127: MS (APCI): 894 (M⁺). Compound 128: MS (APCI): 910 (M⁺). Compound 129: MS (APCI): 910 (M⁺). Compound 130: MS (APCI): 906 (M⁺). Compound 131: MS (APCI): 954 (M⁺). Compound 132: MS (APCI): 878 (M⁺). Compound 133: MS (APCI): 894 (M⁺). Compound 134: MS (APCI): 910 (M⁺). Compound 135: MS (APCI): 906 (M⁺).

TABLE 1
| No. | Compound |
|-----|----------|
| 100 | 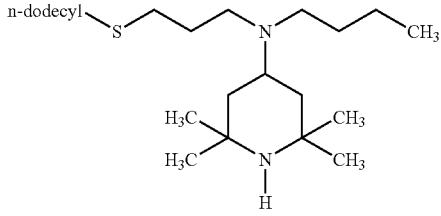 |
| 101 | 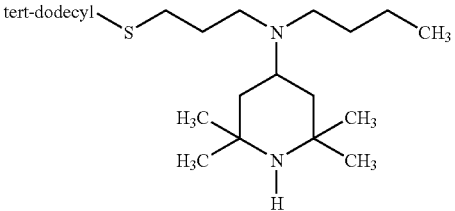 |
| 102 | 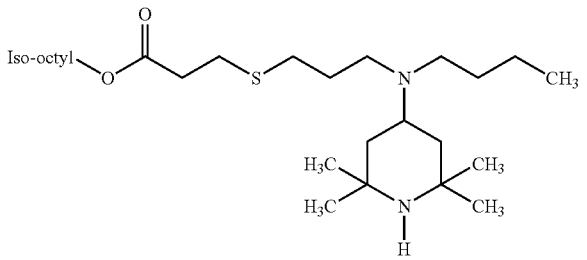 |
| 103 | 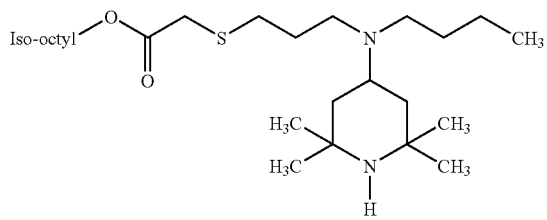 |
| 104 | 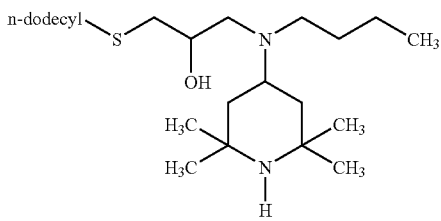 |
| 105 | 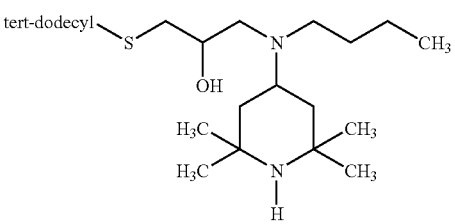 |

TABLE 1-continued
| No. | Compound |
|---|---|
| 106 | 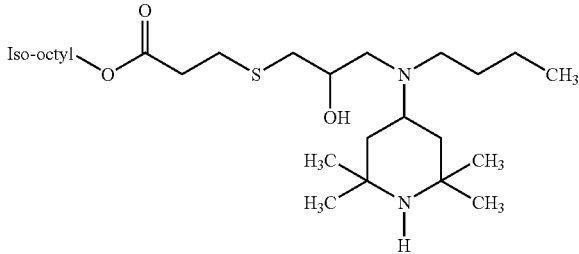 |
| 107 | 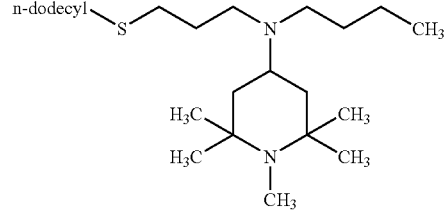 |
| 108 | 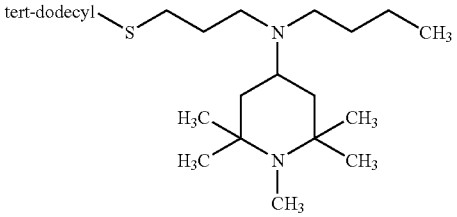 |
| 109 | 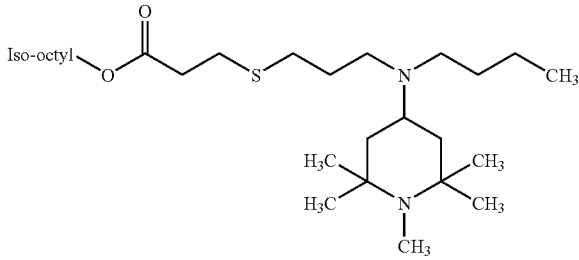 |
| 110 | 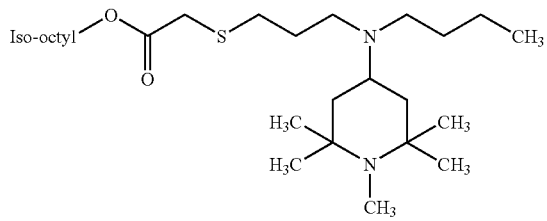 |
| 111 | 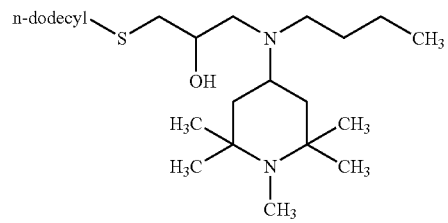 |

TABLE 1-continued
| No. | Compound |
|---|---|
| 112 | 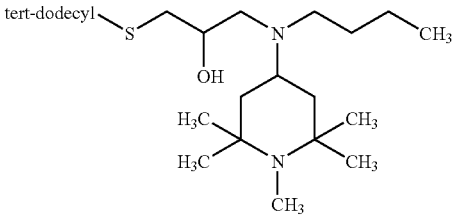 |
| 113 | 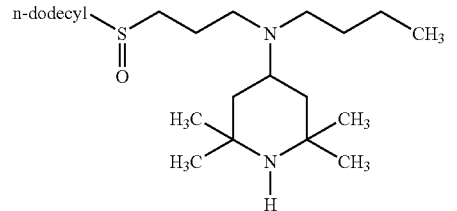 |
| 114 | 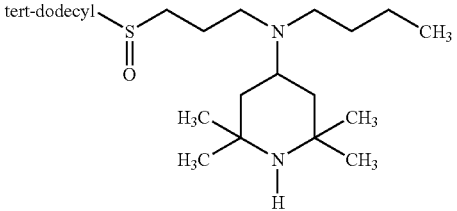 |
| 115 | 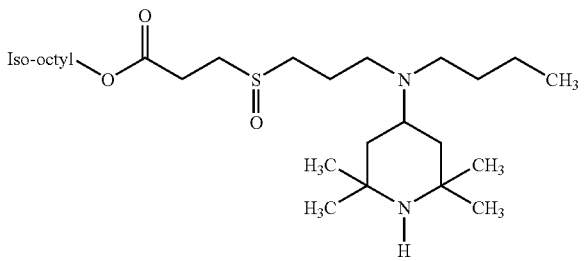 |
| 116 | 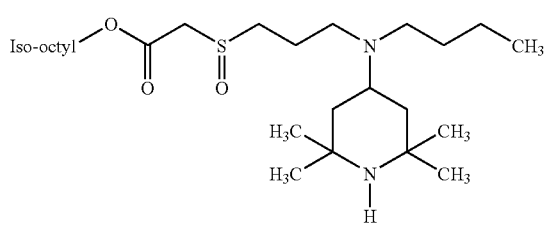 |
| 117 | 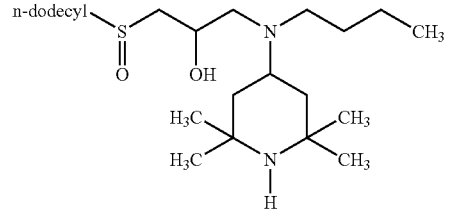 |

TABLE 1-continued
| No. | Compound |
|---|---|
| 118 | 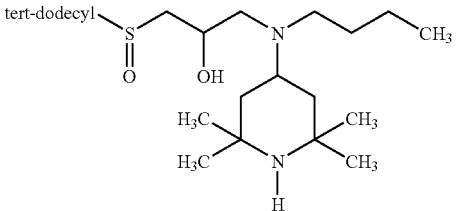 |
| 119 | 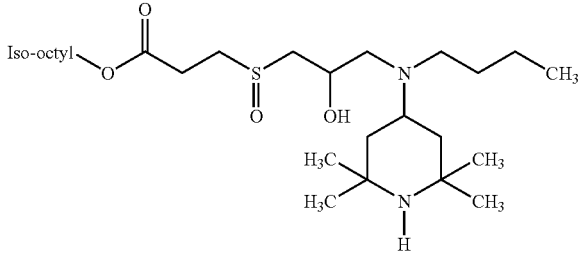 |
| 120 | 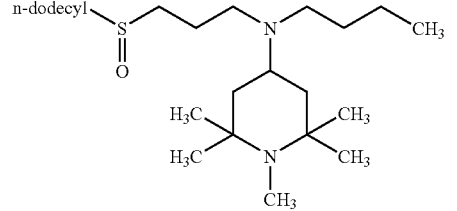 |
| 121 | 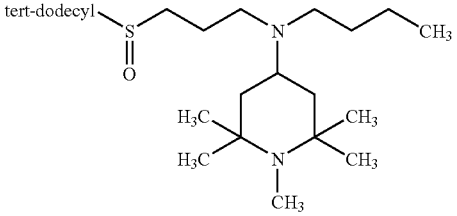 |
| 122 | 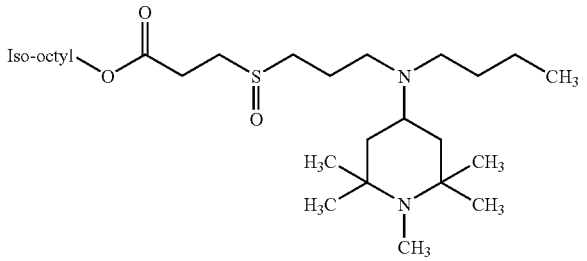 |
| 123 | 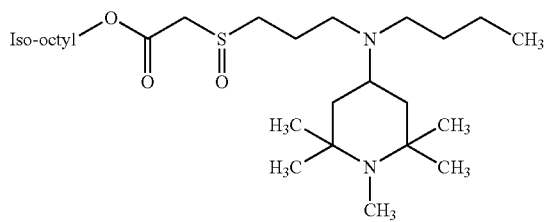 |

TABLE 1-continued

| No. | Compound |
|---|---|
| 124 | n-dodecyl-S(=O)-CH2-CH(OH)-CH2-N(butyl)-(2,2,6,6-tetramethyl-1-methylpiperidin-4-yl) |
| 125 | tert-dodecyl-S(=O)-CH2-CH(OH)-CH2-N(butyl)-(2,2,6,6-tetramethyl-1-methylpiperidin-4-yl) |
| 126 | tert-dodecyl-S-(CH2)3-N[(2,2,6,6-tetramethylpiperidin-4-yl)]-(CH2)6-N[(2,2,6,6-tetramethylpiperidin-4-yl)]-(CH2)3-S-tert-dodecyl |
| 127 | tert-dodecyl-S-(CH2)3-N[(2,2,6,6-tetramethylpiperidin-4-yl)]-(CH2)6-N[(2,2,6,6-tetramethylpiperidin-4-yl)]-(CH2)3-S(=O)-tert-dodecyl |
| 128 | tert-dodecyl-S(=O)-(CH2)3-N[(2,2,6,6-tetramethylpiperidin-4-yl)]-(CH2)6-N[(2,2,6,6-tetramethylpiperidin-4-yl)]-(CH2)3-S(=O)-tert-dodecyl |
| 129 | Iso-octyl-O-C(=O)-CH2CH2-S-(CH2)3-N[(2,2,6,6-tetramethylpiperidin-4-yl)]-(CH2)6-N[(2,2,6,6-tetramethylpiperidin-4-yl)]-(CH2)3-S-CH2CH2-C(=O)-O-Iso-octyl |

TABLE 1-continued

| No. | Compound |
|---|---|
| 130 | tert-dodecyl-S-CH₂CH₂CH₂-N(piperidinyl)-(CH₂)₆-N(piperidinyl)-CH₂CH₂CH₂-S-tert-dodecyl; piperidines are 2,2,6,6-tetramethyl-1-methyl-piperidin-4-yl |
| 131 | tert-dodecyl-S(=O)₂-CH₂CH₂CH₂-N(piperidinyl)-(CH₂)₆-N(piperidinyl)-CH₂CH₂CH₂-S(=O)-tert-dodecyl; piperidines are 2,2,6,6-tetramethyl-1-methyl-piperidin-4-yl |
| 132 | n-dodecyl-S-CH₂CH₂CH₂-N(piperidinyl)-(CH₂)₆-N(piperidinyl)-CH₂CH₂CH₂-S-n-dodecyl; piperidines are 2,2,6,6-tetramethyl-piperidin-4-yl (NH) |
| 133 | n-dodecyl-S(=O)-CH₂CH₂CH₂-N(piperidinyl)-(CH₂)₆-N(piperidinyl)-CH₂CH₂CH₂-S-n-dodecyl; piperidines are 2,2,6,6-tetramethyl-piperidin-4-yl (NH) |
| 134 | n-dodecyl-S(=O)₂-CH₂CH₂CH₂-N(piperidinyl)-(CH₂)₆-N(piperidinyl)-CH₂CH₂CH₂-S(=O)-n-dodecyl; piperidines are 2,2,6,6-tetramethyl-piperidin-4-yl (NH) |
| 135 | n-dodecyl-S-CH₂CH₂CH₂-N(piperidinyl)-(CH₂)₆-N(piperidinyl)-CH₂CH₂CH₂-S-n-dodecyl; piperidines are 2,2,6,6-tetramethyl-1-methyl-piperidin-4-yl |

EXAMPLE 7

Grafting of Polybutadiene

The grafting agents according to the invention which are listed In Table 2 are added to a polybutadiene [low-cis BR BUNA CB 529 T (RTM) from Bayer] pre-stabilised using 0.2% Irganox 1520 (RTM) [4,6-bis(octylthiomethyl)-2-methylphenol]. The actual grafting is accomplished by kneading the rubber in a Brabender Plasticorder at 160° C. and 40 revolutions per minute for 15 minutes. The rubber is then press-moulded in a heated press at 90° C. for 10 minutes to form 2 mm-hick plates. The plates are extracted with acetone at room temperature for 3 days in a Soxhlet apparatus. The rates of incorporation of the grafting agents into the rubber are determined by means of nitrogene determination. The results are compiled in Table 2.

TABLE 2

| Example | Grafting agent | Nitrogene after extraction in ppm and % of the initial value |
| --- | --- | --- |
| 7a[a)] | — | — |
| 7b[a)] | 1% compound 105 | 112 ppm = 15% |
| 7c[b)] | 1% compound 118 | 236 ppm = 38% |
| 7d[b)] | 1% compound 119 | 148 ppm = 22% |
| 7e[b)] | 1% compound 125 | 167 ppm = 25% |

[a)]Comparison Example.
[b)]Example according to the invention.

What is claimed is:

1. A compound of formula I

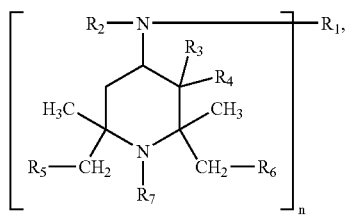  (I)

wherein, when n is 1,
$R_1$ is $C_1$-$C_{25}$alkyl, $C_2$-$C_{18}$hydroxyalkyl, $C_2$-$C_{12}$alkyl interrupted by oxygen or by sulfur; $C_3$-$C_{12}$alkenyl, $C_5$-$C_8$cycloalkyl or $C_7$-$C_{12}$phenylalkyl,
when n is 2,
$R_3$ and $R_4$ are hydrogen or methyl
$R_5$ is hydrogen or methyl,
$R_6$ is hydrogen or methyl,
$R_7$ is hydrogen, $C_1$-$C_8$alkyl, O·, hydroxy, —$CH_2CN$, $C_1$-$C_{18}$alkoxy, $C_5$-$C_{12}$cycloalkoxy, $C_3$-$C_6$alkenyl, $C_7$-$C_9$phenylalkyl unsubstituted or substituted on the phenyl by 1, 2 or 3 $C_1$-$C_4$alkyl;

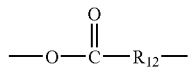

$R_8$ is $C_1$-$C_{18}$alkyl, cyano substituted $C_1$-$C_8$alkyl; or $C_5$-$C_8$cycloalkyl,
$R_9$ is a direct bond or

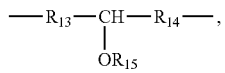

wherein $R_{12}$ is attached to sulfur,
R10 is C2-C3 alkylene or

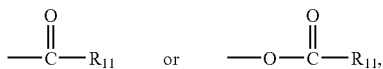

$R_{11}$ is $C_1$-$C_{18}$alkyl, phenyl or $C_3$-$C_{17}$alkenyl,
$R_{12}$ is $C_1$-$C_8$alkylene,
$R_{13}$ is methylene,
$R_{14}$ is methylene,
$R_{15}$ is hydrogen, $C_2$-$C_{18}$alkanoyl or benzoyl,
m is 0, 1 or 2, and
n is 1 or 2.

2. A compound according to claim 1, wherein, when n is 1,
$R_1$ is $C_1$-$C_{18}$alkyl, $C_2$-$C_{12}$hydroxyalkyl, $C_4$-$C_8$alkyl interrupted by oxygen or by sulfur; $C_3$-$C_8$alkenyl, $C_5$-$C_7$cycloalkyl or benzyl,
$R_2$ is $R_8$—$R_9$—S(O)$_m$—$R_{10}$—,
$R_3$ and $R_4$ are hydrogen,
$R_5$ and $R_6$ are hydrogen,
$R_7$ is hydrogen, $C_1$-$C_8$alkyl, O·, hydroxy, —$CH_2CN$, $C_1$-$C_{12}$alkoxy, $C_5$-$C_7$cycloalkoxy, $C_3$-$C_6$alkenyl, benzyl,

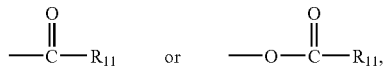

$R_8$ is $C_4$-$C_{18}$alkyl, cyano substituted $C_1$-$C_8$alkyl; or $C_5$-$C_7$cycloalkyl,
$R_9$ is a direct bond or

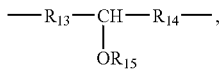

wherein $R_{12}$ is attached to sulfur,
R10 is C2-C3 alkylene or

—$R_{13}$—CH—$R_{14}$—,
      |
      $OR_{15}$ $R_{11}$ is $C_1$-$C_{12}$alkyl, phenyl or $C_3$-$C_{11}$alkenyl,
$R_{12}$ is $C_1$-$C_4$alkylene,
$R_{13}$ is methylene,
$R_{14}$ is methylene,
$R_{15}$ is hydrogen, $C_2$-$C_{12}$alkanoyl or benzoyl,
m is 0, 1 or 2, and
n is 1 or 2.

3. A compound according to claim 1, wherein m is 0 or 1.

4. A compound according to claim 1, wherein $R_3$, $R_4$, $R_5$ and $R_6$ are hydrogen.

5. A compound according to claim 1, wherein, when n is 1,
$R_1$ is $C_2$-$C_{12}$alkyl, $C_2$-$C_8$hydroxyalkyl, $C_4$-$C_8$alkyl interrupted by oxygen; cyclohexyl or benzyl,
$R_2$ is $R_8$—$R_9$—S(O)$_m$—$R_{10}$—,
$R_3$, $R_4$, $R_5$ and $R_6$ are hydrogen,
$R_7$ is hydrogen, $C_1$-$C_4$alkyl, $C_1$-$C_8$alkoxy, cyclohexoxy, benzyl,

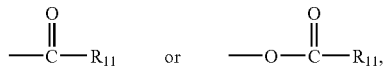

$R_8$ is $C_4$-$C_{14}$alkyl or cyclohexyl,
$R_9$ is a direct bond or

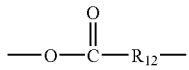

wherein $R_{12}$ is attached to sulfur,
$R10$ is C2-C3 alkylene or

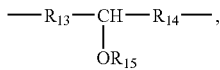

$R_{11}$ is $C_1$-$C_8$alkyl or $C_3$-$C_8$alkenyl,
$R_{12}$ is $C_1$-$C_4$alkylene,
$R_{13}$ and $R_{14}$ are methylene,
$R_{15}$ is hydrogen, $C_2$-$C_4$alkanoyl or benzoyl,
m is 0, 1 or 2, and
n is 1 or 2.

6. A compound according to claim 1, wherein, when n is 1,
$R_1$ is $C_3$-$C_5$alkyl
$R_2$ is $R_8$—$R_9$—$S(O)_m$—$R_{10}$—,
$R_3$, $R_4$, $R_5$ and $R_6$ are hydrogen,
$R_7$ is hydrogen or methyl,
$R_8$ is $C_6$-$C_{14}$alkyl,
$R_9$ is a direct bond or

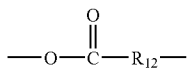

wherein $R_{12}$ is attached to sulfur,
$R10$ is C2-C3 alkylene or

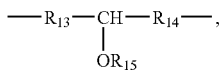

$R_{12}$ is methylene or ethylene,
$R_{13}$ and $R_{14}$ are methylene,
$R_{15}$ is hydrogen,
m is 0, 1 or 2, and
n is 1 or 2.

7. A composition comprising
a) an organic material which is susceptible to oxidative, thermal, dynamic, light-induced and/or ozone-induced degradation, and
b) at least one compound of the formula I according to claim 1.

8. A composition according to claim 7, wherein component (a) is a natural, semi-synthetic or synthetic polymer.

9. A composition according to claim 7, wherein component (a) is a polyolefin, a styrene copolymer or an elastomer.

10. A composition according to claim 7, wherein component (b) is present in an amount of from 0.01 to 10%, based on the weight of component (a).

11. A composition according to claim 7 comprising in addition, besides components (a) and (b), further additives.

12. A composition according to claim 11, comprising as further additives phenolic antioxidants, light-stabilizers, amine-type antioxidants, processing stabilizers, solvents, pigments, dyes, fillers, flow improvers, dispersing agents, plasticizers, vulcanisation activators, vulcanisation accelerators, vulcanisation agents, charge control agents, compatibilizers, adhesion promoters, toughening agents, thixotropic agents, levelling assistants and/or metal passivators.

13. A composition according to claim 11, comprising as further additives phenolic antioxidants, light-stabilizers, amine-type antioxidants, organic phosphites or phosphonites and/or thiosynergistic compounds.

14. A method of stabilizing an organic material against oxidative, thermal, dynamic, light-induced and/or ozone-induced degradation, which comprises incorporating therein, applying thereto or grafting the organic material with at least one compound of the formula I according to claim 1.

15. A method of grafting a compound of the formula I according to claim 1 onto an organic material, which comprises heating, in a processing apparatus for organic materials, a mixture of an organic material and at least one compound of the formula I according to claim 1 above the softening point of the organic material and allowing them to react with one another.

* * * * *

UNITED STATES PATENT AND TRADEMARK OFFICE
CERTIFICATE OF CORRECTION

PATENT NO. : 7,504,510 B2
APPLICATION NO. : 10/543428
DATED : March 17, 2009
INVENTOR(S) : Hans Rudolf Meier et al.

It is certified that error appears in the above-identified patent and that said Letters Patent is hereby corrected as shown below:

In column 37
Line 34, delete "when n is 2"

In column 37
Line 34, insertion of --$R_2$ is $R_8$—$R_9$—$S(O)_m$-$R_{10}$—,-- after "$C_5$-$C_8$cycloalky or $C_7$-$C_{12}$phenylalkyl,"

In column 38
Line 5, replacement of "n is 1 or 2." with "n=1."

In column 38
Line 47, replacement of "n is 1 or 2." with "n=1."

In column 39
Line 20, replacement of "n is 1 or 2." with "n=1."

In column 40
Line 3, replacement of "n is 1 or 2." with "n=1."

Signed and Sealed this

Seventh Day of July, 2009

JOHN DOLL
*Acting Director of the United States Patent and Trademark Office*